(12) United States Patent
Li et al.

(10) Patent No.: US 8,329,166 B2
(45) Date of Patent: Dec. 11, 2012

(54) PLURIPOTENT OLFACTORY STEM CELLS

(75) Inventors: Hung Li, Taipei (TW); Demeral David Liu, Taipei (TW); Woei-Cherng Shyu, Taipei (TW); Shinn-Zong Lin, Hualien (TW)

(73) Assignee: Academia Sinica, Taipei (TW)

( * ) Notice: Subject to any disclaimer, the term of this patent is extended or adjusted under 35 U.S.C. 154(b) by 539 days.

(21) Appl. No.: 11/305,829

(22) Filed: Dec. 16, 2005

(65) Prior Publication Data

US 2007/0141035 A1 Jun. 21, 2007

(51) Int. Cl.
*C12N 5/00* (2006.01)
*C12N 5/074* (2010.01)
*C12N 5/0797* (2010.01)

(52) U.S. Cl. ....... 424/93.7; 435/325; 435/366; 435/368; 435/378

(58) Field of Classification Search .................. 424/93.7; 435/325, 366, 368, 378
See application file for complete search history.

(56) References Cited

U.S. PATENT DOCUMENTS

| 2002/0169102 | A1 | 11/2002 | Frey, II | |
|---|---|---|---|---|
| 2005/0214288 | A1* | 9/2005 | Bell et al. ................... | 424/144.1 |
| 2007/0280989 | A1* | 12/2007 | Shahar et al. ................. | 424/423 |

FOREIGN PATENT DOCUMENTS

WO  WO 03/064601  *  7/2003

OTHER PUBLICATIONS

Lipson et al. Neurotrophic properties of olfactory ensheathing glia. Experimental Neurology, 2003. 180:167-171).*
Salcedo et al (Vascular Endothelial Growth Factor and Basic Fibroblast Growth Factor Induce Expression of CXCR4 on Human Endothelial Cells: Invivo Neovascularization Induced by Stromal-Derived Factor-1α. American Journal of Patrhology, 1999. 154(4):1125-1135) teaches that FGF, VEGF, TNF-α, and SDF-1 are all angiogenesis stimulating mediators (pa.*
"Nasal Polyp." Medline Medical Encyclopedia. (Downloaded from http://www.nlm.nih.gov/medlineplus/ency/article/001641.htm on Jan. 18, 2007).*
Nasal Polyp. McClay. (downloaded from http://www.emedicine.com/ped/topic1550.htm on Jan. 18, 2007).*
Lindvall and Kokala (Stem cell therapy for human brain disorders. Kidney International, 2005. 68:1937-1939).*
Geraerts et al (Therapeutic strategies for Parkinson's disease based on the modulation of adult neurogenesis.Stem. Cells, 2006. Published on line Nov. 2, 2006).*
Snyder and Olanow, Current Opinion in Neurology, 2005. 18:376-385.*
Gerlach et al. Journal of Neurology, 2002. 249 (Supplement 3):III/33-III-35.*
Schwarting et al (Stromal Cell Derived Factor-1 (Chemokine C-X-C Motif Ligand 12) and Chemokine C-X-C Motif Receptor 4 Are Required for Migration of Gonadotropin-Releasing Hormone Neurons to the Forebrain. The Journal of Neuroscience, 2006. 26(25):6834-6840).*
Abe et al, Occipital hypoperfusion in Parkinson's disease without dementia: correlation to impaired cortical visual processing. Journal of Neurology, Neurosurgery, and Psychiatry, 2003:74:419-422).*
Saitoh et al (Gene therapy for Ischemic Brain Diseases, Current Gene Therapy, 2003. 3:49-58).*
Ramer et al, J. Comp. Neurol. 473(1):1-15, 2004.*
Savitz et al, Ann. Neurol. 52:266-275, 2002.*
Roitberg, Neurological Research 26(3):256-264, 2004.*
Wechsler et al, Stroke 34:2081-2082, 2002.*
Modo et al, Brain Res. 958:70-82, 2002.*
Jones et al, NeuroRehabilitation 18:339-351, 2003.*
Woodhall et al, CMLS 60:2241-2253, 2003.*
Zhang et al, Exp. Neurol. 186:112-123, 2004.*
Vincent et al, Glia 41(4):393-403, 2003.*
Liu et al, J. Neurotrauma 21(10):1479-1499, 2004.*
Barnett et al., "Olfactory Ensheathing Cells (OECs) and the Treatment of CNS Injury: Advantages and Possible Caveats," J. Anat., 204:57-67 (2004).
Cao et al., "Olfactory Ensheathing Cells Genetically Modified to Secrete GDNF to Promote Spinal Cord Repair," Brain, 127:535-549 (2004).
Dunning et al., "Superparamagnetic Iron Oxide-Labeled Schwann Cells and Olfactory Ensheathing Cells Can Be Traced In Vivo by Magnetic Resonance Imaging and Retain Functional Properties After Transplantation into the CNS," The Journal of Neuroscience, 24(44):9799-9810 (2004).
García-Alías et al., "Acute Transplantation of Olfactory Ensheathing Cells or Schwann Cells Promotes Recovery After Spinal Cord Injury in the Rat," Journal of Neuroscience Research, 75:632-641 (2004).
Lee et al., "In vivo Magnetic Resonance Tracking of Olfactory Ensheathing Glia Grafted into the Rat Spinal Cord," Experimental Neurology, 187:509-516 (2004).
Lipson et al., "Neurotrophic Properties of Olfactory Ensheathing Glia," *Experimental Neurology*, 180:167-171 (2003).
Moreno-Flores et al., "Olfactory Ensheathing Glia: Drivers of Axonal Regeneration in the Central Nervous System?" Journal o Biomedicine and Biotechnology, 2(1):37-43 (2002).
Sasaki et al., "Identified Olfactory Ensheathing Cells Transplanted into the Transected Dorsal Funiculus Bridge the Lesion an Form Myelin," The Journal of Neuroscience, 24(39):8485-8493 (2004).

* cited by examiner

*Primary Examiner* — Kevin K. Hill
(74) *Attorney, Agent, or Firm* — Occhiuti Rohlicek & Tsao LLP

(57) ABSTRACT

Disclosed is a cultured pluripotent animal cell that is prepared from nasal polyps. Also disclosed are methods for making the cell and methods of treating a brain tissue damage or of promoting cerebral angiogenesis, cerebral neurogenesis, stem cell homing to the brain, neurotrophic factor expression in the brain.

7 Claims, No Drawings

SEQUENCE LISTING

<160> NUMBER OF SEQ ID NOS: 14

<210> SEQ ID NO 1
<211> LENGTH: 21
<212> TYPE: DNA
<213> ORGANISM: Artificial Sequence
<220> FEATURE:
<223> OTHER INFORMATION: Primer -continued

```
<400> SEQUENCE: 1
ttgccagcac aaagacactc c                                             21

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
ctccaaagca aaccgaatac ag                                            22

<210> SEQ ID NO 3
<211> LENGTH: 26
<212> TYPE: DNA
<213> ORGANISM: Artificial Sequence
<220> FEATURE:
<223> OTHER INFORMATION: Primer

<400> SEQUENCE: 3
cagtggacat gtccggtggg acggtc                                        26

<210> SEQ ID NO 4
<211> LENGTH: 27
<212> TYPE: DNA
<213> ORGANISM: Artificial Sequence
<220> FEATURE:
<223> OTHER INFORMATION: Primer

<400> SEQUENCE: 4
ttcttggcaa cggcaacaaa ccacaac                                       27

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
ccacaccgtt tagcggaatg c                                             21

<210> SEQ ID NO 6
<211> LENGTH: 25
<212> TYPE: DNA
<213> ORGANISM: Artificial Sequence
<220> FEATURE:
<223> OTHER INFORMATION: Primer

<400> SEQUENCE: 6
cgggactcta agatgaagtt atggg                                         25

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
gttttggcca gtggtcgtgc ag                                            22

<210> SEQ ID NO 8
<211> LENGTH: 22
```

```
<212> TYPE: DNA
<213> ORGANISM: Artificial Sequence
<220> FEATURE:
<223> OTHER INFORMATION: Primer

<400> SEQUENCE: 8
ccgcttgctc ctgtgagtcc tg                                              22

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
ccgcctcccc catgccgccc                                                 20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
cggggcgggg cttcagctgc                                                 20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
tcacttcgct tcccgcactg                                                 20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
gccgtccatc ttccttcata                                                 20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
gctctcttgg gtgcactgga                                                 20

<210> SEQ ID NO 14
<211> LENGTH: 20
<212> TYPE: DNA
<213> ORGANISM: Artificial Sequence
<220> FEATURE:
<223> OTHER INFORMATION: Primer
```

```
<400> SEQUENCE: 14
caccgccttg gcttgtcaca                                              20
```

PLURIPOTENT OLFACTORY STEM CELLS

BACKGROUND

Pluripotent cells can differentiate into various cell lineages and therefore are useful for treating various degenerative or inherited diseases. Among the pluripotent cells, embryonic stem (ES) cells are believed to hold a great promise. Nonetheless, ethical considerations have hampered the use of human ES cells in research and therapy. Pluripotent cells of non-embryonic origin would circumvent this obstacle. Examples of such non-ES pluripotent cells include adult bone marrow mesenchymal stem cells or stromal cells (Sanchez-Ramos et al., 2000, Exp. Neurol., 164(2):247-256 and Woodbury et al., 2000, J. Neurosci. Res., 61(4):364-370) and umbilical cord blood cells (Galvin-Parton et al., 2003, Pediatr. Transplant. 2003; 7(2):83-85 and Ha et al., 2001 Neuroreport., 2(16):3523-3527). Nonetheless, requirements for in vitro expansion and HLA-matching have limited clinical applications of these cells. Thus, there is a need for alternative pluripotent cells.

SUMMARY

This invention is based, at least in part, on the unexpected discoveries that (i) progenitor cells can be prepared from nasal polyps of an animal; (ii) these cells can differentiate into various cell lineages, including olfactory ensheathing cells and olfactory nerve fibroblasts; and (iii) transplantation of these progenitor cells, olfactory ensheathing cells, or olfactory nerve fibroblasts into the brain can promote cerebral angiogenesis, cerebral neurogenesis, stem cell homing to the brain, or neurotrophic factor expression in the brain.

Accordingly, one aspect of this invention features a method of preparing a pluripotent cell composition by (i) obtaining an tissue from a nasal polyp of an animal, either a human or a non-nonhuman animal; (ii) culturing the tissue under a condition to allow cell migration; and (iii) collecting cells that migrate from the cultured tissue to acquire a pluripotent cell composition. The majority of the colleted cells are p75$^+$, S100$^+$, or GFAP$^+$. These isolated cells can differentiate into, among others, olfactory ensheathing cells and olfactory nerve fibroblasts, and therefore are named olfactory stem cells or olfactory ensheathing progenitor cells.

This invention also provides a pluripotent cell composition that is prepared according to the just-described method. The cell composition can contain the olfactory ensheathing progenitor/stem cells, olfactory ensheathing cells, or olfactory nerve fibroblasts. All of these three types of cells can differentiate into neural and vascular tissues. Thus, they can be used for treating brain tissue damage.

Accordingly, another aspect of this invention features a method for treating a brain tissue damage by intracerebrally administering to a subject (either a human or a non-nonhuman animal) in need thereof an effective amount of a cell composition that contains olfactory ensheathing progenitor cells, olfactory ensheathing cells, or olfactory nerve fibroblasts. The brain tissue damage can be caused by cerebral ischemia or a neurodegenerative disease, such as Alzheimer's disease, epilepsy, Huntington's disease, Parkinson's disease, or Spinocerebellar disease. The olfactory ensheathing progenitor cells, olfactory ensheathing cells, or olfactory nerve fibroblasts can be prepared from a nasal polyp of an animal by a process described above. The olfactory ensheathing cells or olfactory nerve fibroblasts can also be prepared according to methods known in the art. The cells to be transplanted to a subject can be autologous or heterologous to the subject.

The term "treating" refers to administration of a composition to a subject, who is suffering from or is at risk for developing brain tissue damage or a disorder causing such damage, with the purpose to cure, alleviate, relieve, remedy, prevent, or ameliorate the damage/disorder, the symptom of the damage/disorder, the disease state secondary to the damage/disorder, or the predisposition toward the damage/disorder. The term "effective amount" refers to an amount of the composition that is capable of producing a medically desirable result, e.g., as described above, in a treated subject. The treatment method can be performed alone or in conjunction with other drugs or therapies.

The above-mentioned olfactory ensheathing progenitor cells, olfactory ensheathing cells, or olfactory nerve fibroblasts can also be intracerebrally administered at an effective amount to a subject in need thereof to promote cerebral angiogenesis, cerebral neurogenesis, homing of stem cells to the brain, or increase the level of a neurotrophic factor in the brain. The subject may or may not have a brain tissue damage.

For promoting cerebral angiogenesis, the method can further include measuring a level of cerebral angiogenesis in the subject before and after administering the composition to confirm promotion of cerebral angiogenesis. The measurement can be performed by standard brain imaging techniques, such as computed tomography (CT), Doppler ultrasound imaging (DUI), magnetic resonance imaging (MRI), and proton magnetic resonance spectroscopy ($^1$H-MRS). For promoting neurogenesis, the method can further include measuring a level of neurogenesis in the brain of the subject before and after administering to confirm promotion of neurogenesis by, e.g., standard neurological behavioral measurements including those described in the examples below. For increasing the level of a neurotrophic factor (e.g., SDF-1, BDNF, GDNF, NGF, TGF-$\beta$, FGF-II, or VEGF), the method further includes measuring a level of the neurotrophic factor in the brain of the subject before and after administering to confirm an increase.

The details of one or more embodiments of the invention are set forth in the description below. Other features, objects, and advantages of the invention will be apparent from the description and from the claims.

DETAILED DESCRIPTION

The present invention relates to isolated or cultured olfactory stem/ensheathing progenitor cells. These cells are pluripotent as they can differentiate into various cell lineages and have phenotypes characteristic of fibroblasts and astrocytes. The predominant cell morphology is spindle shape in cultures. The majority of the cells co-express p75/GFAP, p75/S100, GFAP/fibronectin, or GFAP/S100. The cells also express and secret SDF-1, G-CSF, CXCR4, SCF, c-kit, and G-CSF-R.

The pluripotent cells can be isolated from a nasal polyp, a jelly-like overgrowth of the lining of sinus of an animal, according to the method described in Example 1 below or analogous methods known in the art. The cells can be maintained in a DMEM/F12 medium containing a B27 medium supplement, 10% FCS, and 1% (100 U/ml) penicillin/streptomycin. The cells can be further enriched based on their antignecity and morphology using any suitable cell separation techniques known in the art. To more rapidly enrich a large amount of cells, one can use the fluorescence-activated cell sorting (FACS) techniques. For example, anti-p75, GFAP, S100, or fibronectin monoclonal antibodies linked with different fluorescent labels can be used to enrich cells that are positive for the markers.

To test the pluripotency of the cells, one can use any suitable in vitro or in vivo methods. For example, one can transplant the cells to a rat model of complete spinal cord transection injury and examine HRP-labeled corticospinal tract or hindlimb function in the manner described in Example 1 below. Alternatively, one can transplant the cells to the brain of an animal and examine whether the cells differentiate into neurons, glial, or vascular endothelial cells according to the method described in Example 5 below. After confirmation, the cells can be used in a variety of ways, including treating degenerative diseases. As the cells are of non-embryonic origin (i.e., somatic), using them does not entail ethical considerations of human embryo manipulation.

The above-described method can be used to prepare olfactory ensheathing cells (OECs). Conventionally, OECs, a unique glial cell population, are isolated from an olfactory bulb, a distinct outgrowth from the forebrain. The outgrowth consists of a bulbous enlargement of the end of the olfactory nerve on the under surface of the frontal lobe of each cerebral hemisphere and is just above the nasal cavity. In a olfactory bulb, OECs are those firstly encountered by newly formed axons of olfactory receptor neurons. They guide the newly formed axons growing and synapasing with olfactory nerves from the nasal cavity to the central nervous system. Because of this guiding ability, murine OECs have been used to repair defective myelin and injured spinal cord in experimental animals suffering from spinal cord injury. However, clinical uses of human OECs are limited, if not impossible. Indeed, due to the central nerve system location of OECs, isolating human OECs from an olfactory bulb is a daunting task and can damage the olfactory system or the brain. In rodents, nasal lamina propria layers of nasal mucosa have been exploited as an alternative source of OECs.

The preparation method of this invention allows one to prepare OEC's from nasal polyps, which are easily accessible, thereby providing a practical source for OECs. The OECs prepared by this method have the ability to repair spinal cord injury or to differentiate into neurons, glial, or vascular endothelial cells. One can use suitable methods, including those descried in Example 1 or 5 below, to confirm the potency of the cells.

Confirmed olfactory OECs, as well as ensheathing progenitor cells or olfactory nerve fibroblasts, can be stored by standard methods. They can be administered intracerebrally to a subject in need thereof.

Within the scope of this invention is a method of treating brain tissue damage or alleviate the symptom of the disorder in a subject. The method includes identifying a subject suffering from or being at risk for developing brain tissue damage. The subject can be a human or a non-human mammal, such as a cat, a dog, or a horse. Examples of the brain tissue damage includes those caused by a cerebral ischemia (e.g., chronic stroke) or a neurodegenerative disease (e.g., Parkinson's disease, Alzheimer's disease, Spinocerebellar disease, or Huntington's disease). A subject to be treated can be identified by standard techniques for diagnosing the conditions or disorders of interest. The treatment method entails administering to a subject in need thereof an effective amount of the above-described olfactory ensheathing progenitor cells, olfactory ensheathing cells, or olfactory nerve fibroblasts. In general, $1\times10^4$ to $2\times10^7$ cells are administered. Multiple sites can be used depending on the site and nature of particular damage. Example 3 below describes approximate coordinates for administering cells in a rat ischemia model. Coordinates for other disorders in other species can be determined accordingly based on comparative anatomy.

The therapeutic effects of cells can be accessed according to standard methods (e.g., those described in Examples 3-9 below). To confirm efficacy in promoting cerebrovascular angiogenesis, one can examine the subject before and after the treatment by standard brain imaging techniques, such as computed tomography (CT), Doppler ultrasound imaging (DUI), magnetic resonance imaging (MRI), and proton magnetic resonance spectroscopy ($^1$H-MRS). For example, $^1$H-MRS represents a non-invasive means to obtain biochemical information correlated to brain metabolic activity (Lu et al., 1997, Magn. Reson. Med. 37, 18-23). This technique can be applied to evaluate the metabolic changes involved in cerebral ischemia with or without cell transplantation. For example, it can be used to study the N-acetylaspartate (NAA) concentration in the brain, a marker of neuronal integrity. Although NAA redistribution and trapping in neuronal debris limits its use as a quantitative neuronal marker, decreases in brain NAA concentration in cerebral ischemia can be considered as an index of neuronal loss or dysfunction (Demougeot et al., 2004, J. Neurochem. 90, 776-83). Therefore, an NAA level, measured by $^1$H-MRS, is an useful indicator for following the effect of cell transplantation after cerebral ischemia.

One can also measure the expression level of a neuronal marker, a vascular marker, a glial marker, a trophic factor, or a cell death-related protein in a sample (e.g., cerebrospinal fluid) obtained from the animal before or after administration to confirm efficacy. The expression level can be determined at either the mRNA level or the protein level. Methods of measuring mRNA levels in a tissue sample or a body fluid are well known in the art. To measure mRNA levels, cells can be lyses and the levels of mRNA in the lists, whether purified or not, can be determined by, e.g., hybridization assays (using detectably labeled gene-specific DNA or RNA probes) and quantitative or semi-quantitative RT-PCR (using appropriate gene-specific primers). Alternatively, quantitative or semi-quantitative in situ hybridization assays can be carried out on tissue sections or unlysed cell suspensions using detectably (e.g., fluorescent or enzyme) labeled DNA or RNA probes. Additional mRNA-quantifying methods include the RNA protection assay (RPA) method and the serial analysis of gene expression (SAGE) method, as well as array-based technologies.

Methods of measuring protein levels in a tissue sample or a body fluid are also well known in the art. Some of them employ antibodies (e.g., monoclonal or polyclonal antibodies) that bind specifically to a target protein. In such assays, the antibody itself or a secondary antibody that binds to it can be detectably labeled. Alternatively, the antibody can be conjugated with biotin. Its presence can be determined by detectably labeled avidin (a polypeptide that binds to biotin). Combinations of these approaches (including "multi-layer sandwich" assays) can be used to enhance the sensitivity of the methodologies. Some protein-measuring assays (e.g., ELISA or Western blot) can be applied to body fluids or to lysates of cells, and others (e.g., immunohistological methods or fluorescence flow cytometry) can be applied to histological sections or unlysed cell suspensions. Appropriate labels include radionuclides (e.g., $^{125}$I, $^{131}$I, $^{35}$S, $^3$H, or $^{32}$P), enzymes (e.g., alkaline phosphatase, horseradish peroxidase, luciferase, or β-glactosidase), fluorescent/luminescent agents (e.g., fluorescein, rhodamine, phycoerythrin, GFP, BFP, and Qdot™ nanoparticles supplied by the Quantum Dot Corporation, Palo Alto, Calif.). Other applicable methods include quantitative immunoprecipitation or complement fixation assays.

Based on the results from the assays described above, an appropriate dosage range and administration route can be determined. The dosage required depends on the choice of the route of administration; the nature of the formulation; the nature of the patient's illness; the subject's size, weight, surface area, age, and sex; other drugs being administered; and the judgment of the attending physician. Dosage variations are necessary in view of the different efficiencies of various routes of administration. The variations can be adjusted using standard empirical routines for optimization as is well understood in the art. For example, the cells can be administered (e.g., intracerebrally) to a subject at $1 \times 10^4$ to $2 \times 10^7$/time, preferably at $1 \times 10^5$ to $1 \times 10^7$/time, or more preferably at $5 \times 10^5$ to $5 \times 10^6$/time. To minimize or avoid host rejections, the cells are preferably autologous to the subject.

Both heterologous and autologous olfactory ensheathing progenitor cells, olfactory ensheathing cells, or olfactory nerve fibroblasts can be used. In the former case, HLA-matching should be conducted to avoid or minimize host reactions. In the latter case, autologous cells can be enriched and purified from a subject and stored for later use.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Further, any mechanism proposed below does not in any way restrict the scope of the claimed invention.

EXAMPLE 1

Human olfactory ensheathing progenitor cells/olfactory ensheathing cells/olfactory nerve fibroblasts (hOEPs/OECs/ONFs) were prepared from surgical samples of nasal polyps.

Human nasal polyp samples (5 mm$^3$, 1 gm in weight) were obtained and collected in sterile boxes containing the Hanks' balanced salt solution (HBSS; Gibco/BRL). Protocols for sampling human nasal polyps were approved by the Institutional Review Board of Tzu-Chi University Hospital and written informed consent was obtained from each patient.

Each nasal polyp tissue was carefully dissected into small pieces under a dissecting microscope and placed in a phosphate-buffered solution at room temperature. Within 24 hours, the tissue pieces were grounded with a dissection scalpel before being transferred into 10 ml of a DMEM (Dulbecco's Modified Eagle Medium)/F12 medium containing trypsin and EDTA. The resulting mixture was incubated in a shaking water bath at 37° C. for 5 minutes. The grounded tissue were then rinsed with a DMEM/F12 solution, triturated with a fire-polished Pasteur pipette, and collected by centrifugation at 600 g for 10 minutes. The resulting pellet was resuspended in a DMEM/F12 medium containing a B27 medium supplement, 10% FCS, and 1% (100 U/ml) penicillin/streptomycin at 300,000 cells per ml. The resuspended tissue samples were placed in a 75 cm$^2$ flask coated with poly-L-lysine and incubated under 5% $CO_2$ at 37° C. They were left undisturbed for 5-7 days to allow for migration of the cells from the samples. Further passage of these primary cells was performed once a week for three to four weeks. It was found that the cells attached to the flask and spread out slowly. The predominant cell morphology was spindle shape with both flattened fibroblast-like and astrocyte-like pattern.

Immunocytochemical study was performed on the cells using various antibodies, including that specifically bind to low-affinity nerve growth factor receptor (p75, 1:100, Chemicon), glial fibrillary acidic protein (GFAP, 1:200, Sigma), fibronectin (FN, 1:1000, Molecular Probe), S100 (1:1000, Dako), oligodendrocyte marker 4 (O4, 1:100, Chemicon), Stromal cell-derived factor 1 (SDF-1, 1:200, R&D), CXC receptor type 4 (CXCR4, 1:100, Chemicon), Granulocyte-Colony Stimulating Factor (G-CSF, 1:100, Abcam), Granulocyte-Colony Stimulating Factor receptor (G-CSF-R, 1:100, Novus), Stem Cell Factor (SCF, 1:200), anti-c-Kit (1:300), Neurofilament-200 (NF-200, 1:300, Sigma), βIII-tubulin (Tuj-1, 1:200, Chemicon), Microtubular associate protein-2 (MAP-2, 1:300, BM), or Neuronal nucleus (Neu-N, 1:300, Chemicon). The cells were plated on a poly-L-lysine-coated chambered glass slide at a standard density and allowed to grow at 37° C. and 5% $CO_2$ for 24 hours. The antigenicity of cells population were quantified by a method modified from that described in Edmund, 2003, Glia. 41:224-236. A random field of view was selected at 200× magnification with a UV filter. Images were captured and assessed using a Spot digital camera (Diagnostic Instruments) and Northern Eclipse 5.0 software (Empix Imaging).

This immunocytochemistry analysis demonstrated that the majority of the cells co-expressed p75/GFAP, p75/S100, GFAP/fibronectin, or GFAP/S100. It was found that 94%±2.8%, 95%±3.3%, and 70%±2.1% of the cells expressed S100, p75, and GFAP, respectively.

To confirm the repairing ability of these cells, an aliquot of the cells was transplanted to complete transection injury rat models of spinal cord. More specifically, the model rats were divided into three groups. Each rat in the experimental group received the cells described above at the T8 level by a standard method. Rats in the other two control groups received a culture medium or did not receive any cell or medium. Eight weeks later, HRP was injected into the motor cortex of each rat and the anterograde tracing study was performed. Two days later, the spinal cord was collected and examined. HRP-labeled corticospinal tract (CST) were found across the transection site and in the caudal side of spinal cord of the rat in the experimental. These CST fibers extended to the lumbar spinal cord and most of them were observed in the white matter. No HRP-labeled fiber below the transection site was found in rats in the two control groups although labeled fibers were found in the proximal stump of the spinal cord.

The hindlimb function was also evaluated with BBB scale. It was found that the rats in the experimental group showed a statistically significant improvement 3 weeks after transplantation as compared with those in the two control groups. The difference persisted and became more significant up to 8 weeks. Immunohistochemistry study also confirmed survival of the transplanted human cells, new myelin formation, and regeneration of axon along the myelin sheath.

Unexpectedly, it was found that the cells prepared from nasal polyp could be transplanted into different species successfully without using immuosuppression drugs and that the cells survived much longer time than conventional olfactory ensheathing cells. For example, the cells described in Lakatos 2003 could survive for only 2-10 days (Lakatos A, Brain 2003; 126:598-609). Also, compared with rodent olfactory bulb olfactory ensheathing cells, the cells described herein could achieve a much better hindlimb locomotor's function (BBB scale about 11). These results suggest that the cells prepared from nasal polyp according to the above process contain olfactory ensheathing progenitor cells and possess the regeneration ability of conventional olfactory ensheathing cells prepared from olfactory bulbs.

EXAMPLE 2

Double immunofluorescent staining was performed to examine the expression of SDF-1, G-CSF, and their receptors CXCR4 and G-CSF-R in cells prepared by the method described above. It was found that the cells co-expressed the following pair of proteins: SDF-1 and GFAP, SDF-1 and p75, CXCR4 and GFAP, CXCR4 and p75, G-CSF and GFAP, G-CSF and p75, G-CSF-R and GFAP, G-CSF-R and p75, SCF and GFAP, SCF and p75, c-kit and GFAP, and c-kit and p75.

Western blot was also performed to examine the expression of SDF-1, G-CSF, CXCR4, and G-CSF-R in the above-described cells that were treated with hypoxia-reoxygenation. Briefly, cells were placed in a hypoxic chamber (Bug Box, Ruskinn Technology, UK) at 37° C. for 12 hours. The chamber was continuously flushed with 95% $N_2$-5% $CO_2$ to maintain a gas phase $PO_2$ of <1 mmHg (OM-14 oxygen monitor; SensorMedics Corporation, Yorba Linda, Calif.). After each hypoxic treatment, the cells were returned to a 37° C. normoxic incubator (95% air-5% $CO_2$) for different time durations (30 minutes, 1 hour, 4 hours, 12 hours, 24 hours, and 48 hours) of reoxygenation. Cell samples were then collected at each time point and stored at −80° C. For Western blot, the samples were lysed in a buffer containing 320 mM sucrose, 5 mM HEPES, 1 μg/ml leupeptin, 1 μg/ml aprotinin. The resulting lysate were centrifuged at 13,000 g for 15 minutes. The pellet was resuspended in a sample buffer (62.5 mM Tris-HCl, 10% glycerol, 2% SDS, 0.1% bromophenol blue, and 50 mM DTT) and subjected to SDS-polyacrylamide gel (4-12%) electrophoresis. Proteins were then transferred to a Hybond-P nylon membrane followed by incubation with appropriately diluted antibodies to SDF-1 (1:200, R&D), CXCR4 (1:100, Chemicon), SCF (1:200), c-Kit (1:300), G-CSF (1:100, Abcam), G-CSF-R (1:100, Novus), activated Akt (1:200; Calbiochem), activated ERK1/2 (1:200; Santa-Crutz), activated p38 (1:200; Santa-Crutz), activated JNK (1:200; Santa-Crutz), or β-Actin (1:2000, Santa-Crutz). Membrane blocking, primary and secondary antibody incubations, and chemiluminescence reactions were conducted according to the manufacturer's protocol. The intensity of each detected band was quantified using a Kodak Digital Science 1D Image Analysis System (Eastman Kodak, Rochester, N.Y.). It was found that the protein level of SDF-1, CXCR4, G-CSF, G-CSF-R, SCF, or c-kit increased in the cells in a time-dependent manner four hours after hypoxia-reoxygenation treatment compared with control cells that were not subjected to the treatment.

It was also found that the ratio of p-Akt and p-ERK1/2/Actin protein reached a peak level of about a two-fold increase in treated cells compared with the control cells. The levels of p38 and JNK showed no statistically significant difference between treated cells and control cells.

The above assay was repeated except that cells were pre-treated with specific ERK1/2 pathway inhibitor PD98059 (10 μM) (Cell Signaling Technology, Inc.) and Akt pathway inhibitor wortmannin or LY294002 (10 nM, Calbiochem). These inhibitors suppress enzyme binding so as to block the transcriptional signal of ERK1/2 and Akt. It was found that expression of SDF-1 stayed at the control level. This result demonstrates that activation Akt and ERK1/2 is involved in the change of SDF-1 level.

EXAMPLE 3

Cells prepared according to the process described in Example 1 were transplanted to rats having cerebral ischemia. Their effects on neurological behavior of the rats were examined.

Adult male Sprague-Dawley rats (weighing 250-300 g) were subjected to three-vessel ligation (MCA ligation). All surgical procedures were performed by sterile/aseptic techniques in accordance with Institutional guidelines as previously described in Shyu et al. Circulation 2004; 110:1847-54. One week after this brain ischemia procedure, the rats (weight>300 g) were divided into two groups and anesthetized with chloral hydrate (0.4 g/kg, ip). The rats in one group (treated group) were transplanted with cells and those in the other group (control group) were mock-transplanted.

Cells to be transplanted were cultured in a DMEM medium containing 10% FCS in a humidified atmosphere of 5% $CO_2$/95% air and antibiotics at 37° C. To trace the cells, the cells were incubated with 1 μg/mL bis-benzimide (Hoechst 33342; Sigma, U.S.A.), which labels nuclei with blue color fluorescence, for 5 hours at 37° C. prior to transplantation. The labeled cells were collected and washed in PBS three times. Nucleated cells were counted using a cytometer to ensure an adequate number for transplantation. The cells (approximately $1 \times 10^6$ cells in 3-5 μl of the DMEM medium) were then injected intracerebrally to the above-described rats via a 26-gauge Hamilton syringe into 3 cortical areas adjacent to the right MCA, 3.0 to 5.0 mm below the dura according to the method described in Shyu et al., 2004, Circulation 110:1847-54.

Behavioral tests were performed 5 days before the cerebral ischemia, and at Days 1, 7, 14, and 28 after cell transplantation. The tests measured body asymmetry, locomotor activity, and grip strength in treated rats (n=10) and control rats (n=10). The behavioral measurement scores were all normalized by the baseline scores.

A body asymmetry trial was carried out to assess body swing before and after MCA ligation the rats according the method described in Shyu et al. mentioned above. Since cerebral ischemia causes imbalanced motor activity, all of the rats developed significant body asymmetry: turning contralateral to the side of the ischemic brain on day 1 following cerebral ischemia. From Days 14 to 28 after treatment, the rats transplanted with the cells exhibited significantly reduced body asymmetry in comparison with the control rats.

Locomotor activity was also examined before and after cerebral ischemia in all rats (Shyu et al. 2004, Circulation 110:1847-54). It was found that rats transplanted with the cells exhibited significantly increased vertical activity, vertical movement time, and the number of vertical movements between Days 14 and 28 after cerebral ischemia in comparison with the control rats.

Grip strength was analyzed before and 28 days after the transplantation using a Grip Strength Meter (TSE-Systems, Germany) by a method modified from that described in Dunnett et al. 1998, Neurosci. Lett. 246:1-4. The grip strength ratio of each forelimb was measured separately and calculated as the ratio between the mean strength out of 20 pulls of the side contralateral to the ischemia and that of ipsilateral side. In addition, the ratio of grip strength post-transplantation and pre-transplantation were also calculated and the changes were presented as a percentage of the pre-treatment value. The results revealed that the treated rats had higher ratios of grip strength than those in the control group.

EXAMPLE 4

Western blot and RT-PCR were conducted to examiner expression of neurotrophic factor, antiapoptotic protein, and synatic plasticity-related protein in the above-described rats.

The rats were anesthetized with chloral hydrate (0.4 g/kg, ip) at Days 3, 7, 14, and 28 after the transplantation. Ischemic cortical and striatal areas were evacuated and put on ice immediately. The brain tissues were then homogenized by a plastic hemogenizer. Total protein was isolated and subjected to Western blot analysis in the manner described Issa, 2005, Angiogenesis 8:53-6 using specific antibodies against BDNF, GDNF, VEGF, SDF (1:200), SCF (1:200), G-CSF (1:100), Bcl-2 (1:200; Santa-Crutz), Bcl-xL (1:200; Transduction Laboratories), Bad (1:200; Santa-Crutz), Bax (1:200; Transduction Laboratories), GAP-43 (synapse, 1:300, Chemicon), Synaptophysin (1:50, DAKO), HuC/D (1:200, Clonegene), or Actin (1:2000, Santa-Crutz).

It was found that the levels of SDF-1, GDNF, and BDNF in the treated rats (n=7) were higher than those in control rats (n=7). The ratio of SDF-1, GDNF, or BDNF to GAPDH peaked at about a 2 to 3.5-folds 3 to 7 days after the transplantation. These results demonstrate that the improvement in neurological function in the treated rats correlated with expression of the three factors.

The expression of neurotrophic factors SDF-1, BDNF, GDNF, NGF, TGF-β, FGF-II and VEGF were evaluated by quantitative RT-PCR (QRT-PCR) and conventional RT-PCR. RNA was prepared using a RNeasy® kit (Qiagen). Specific primers used are summarized in Table 1 below.

TABLE 1

Sequence of PCR primers for neurotrophic factors

| Factors | Sequence | PCR fragment |
|---|---|---|
| SDF-1 | sense-TTGCCAGCACAAAGACACTCC (SEQ ID NO: 1) anti-sense-CTCCAAAGCAAACCGAATACAG (SEQ ID NO: 2) | 243 bp |
| BDNF | sense-CAGTGGACATGTCCGGTGGGACGGTC (SEQ ID NO: 3) anti-sense-TTCTTGGCAACGGCAACAAACCA CAAC (SEQ ID NO: 4) | 533 bp |
| GDNF | sense-CCACACCGTTTAGCGGAATGC (SEQ ID NO: 5) anti-sense-CGGGACTCTAAGATGAAGTTATG GG (SEQ ID NO: 6) | 638 bp |
| NGF | sense-GTTTTGGCCAGTGGTCGTGCAG (SEQ ID NO: 7) anti-sense-CCGCTTGCTCCTGTGAGTCCTG (SEQ ID NO: 8) | 498 bp |
| TGF-β | sense-CCGCCTCCCCCATGCCGCCC (SEQ ID NO: 9) anti-sense-CGGGGCGGGGCTTCAGCTGC (SEQ ID NO: 10) | 710 bp |
| FGF-II | sense-TCACTTCGCTTCCCGCACTG (SEQ ID NO: 11) anti-sense-GCCGTCCATCTTCCTTCATA (SEQ ID NO: 12) | 252 bp |
| VEGF | sense-GCTCTCTTGGGTGCACTGGA (SEQ ID NO: 13) anti-sense-CACCGCCTTGGCTTGTCACA (SEQ ID NO: 14) | 431 bp |

The relative amount of target mRNA was determined by QRT-PCR using SYBR Green following the manufacturer's instructions (Roche Diagnostics) and normalized against the level of GAPDH, an internal standard. The whole procedure of QRT-PCR was modified from that described in Luo et al. 2004, Respir. Res. 5:20. The conventional RT-PCR was performed according to the method described in Shyu et al. 2004, Cell Mol. Neurobiol. 2004; 24:257-68. It was found that the treated rats had significantly higher levels of SDF-1, GDNF, and BDNF than the control rats. The results were consistent with the Western blot results described above.

It is known that SDF-1 and its receptor CXCR4 provide trophic support to both embryonic and mature neurons (Hill et al., 2004, J. Neuropathol. Exp. Neurol. 63:84-96; Zheng et al., 1999, J. Neuroimmunol. 98:185-200; and Evert et al., 2001 J. Neurosci. 21:5389-96. Furthermore, SDF-1 acts as a potent chemo-attractant for hematopoietic stem cells (HSCs) (Jo et al., 2000, J. Clin. Invest., 105:101-11 and Shirozu et al., 1995, Genomics, 28:495-500). G-CSF and SCF also mobilize HSCs from bone marrow into peripheral blood (PB) (Demetri, Blood. 1991; 78:2791-808; Hematti, Stem Cell 2004; 22:1062-9). The above results suggest that transplanted cells can promote homing of HSCs to the brain.

EXAMPLE 5

Double fluorescent immunohistochemistry and laser-scanning confocal microscopy were performed to determine if the above-described transplanted cells could differentiate into neurons, glial, or vascular endothelial cells at ischemic sites in the brain.

Adult male Sprague-Dawley rats (weighing 250-300 g) were subjected to three-vessel ligation (MCA ligation) and transplantation (treated) or mock-transplantation (control) in the manner described above. At Day 28 after cells transplantation, each of the treated rats (n=10) was anesthetized with chloral hydrate (0.4 g/kg, ip) and the brain was fixed by transcardial perfusion with saline followed by perfusion and immersion of 4% paraformaldehyde according to the method described in Shyu et al. 2004, Circulation, 110:1847-54. Brain sections were then obtained by standard methods. The sections were then examined for the expression of neuron, glial, or vascular endothelial cell specific markers by immunofluorescent staining. Cell-type specific markers used included GFAP (1:400, Sigma), von Willebrand factor (vWF, 1:300, Sigma), Nestin (1:400, Chemicon), microtubule-associated protein 2 (MAP-2, 1:200, BM), neuronal nuclei (Neu-N, 1:300, Chemicon), CXCR4 (1:100, Santa-Crutz), and Doublecortin (Dcx, 1:300). As nuclei of the transplanted cell had been labeled with bis-bezimide, they emitted blue fluorescence upon irritation by an excitement light. The number of cells stained with both bisbenzimide and a cell-type specific marker was determined according to the method described in Li et al. 2002, Neurology, 59:514-23.

It was found that some bis-benzimide labeled cells also expressed GFAP, MAP-2, and Neu-N in the penumbra. Co-localization of bisbenzimide-labeled cells and antibodies for Nestin was also found in the peri-infarcted area. Percentages of bisbenzimide-labeled cells that are positive for MAP-2, GFAP, Neu-N, and Nestin were about 5%, 8%, 6%, and 2%, respectively. These results indicate that the transplanted cells trans-differentiated and generated new neural and vascular tissues to repair injured areas of the brain.

EXAMPLE 6

Effects of the above-described transplantation on mobilized peripheral blood stem cells (MPBSCs) migration and neural synaptic formation were examined. Double immunostaining of MPBSC specific markers CXCR4 and Dcx was performed on the brain sections prepared according to the method described above. The sections were examined by confocal microscopy.

It was found that the majority of the transplanted cells in the penumbric region were co-localized with CXCR4. Dcx was found to be around the ischemic region. These results suggest that MPBSCs migrated to the penumbric area and repair the injured brain. Furthermore, synaptic formation between the transplanted cells and host cells was demonstrated by the colocalization analysis of synaptophysin.

EXAMPLE 7

Effects of the above-described transplantation on cerebral angiogenesis and vascular remodeling were evaluated.

Rats were subjected to three-vessel ligation (MCA ligation) and transplantation (treated) or mock-transplantation (control) in the manner described above. At Day 28 after transplantation, cerebral microcirculation was analyzed. Each rat was administered intravenously FITC-dextran, a fluorescent plasma marker, and observed under a Carl Zeiss, Axiovert 200M fluorescent microscope according the method described in Morris et al. 1999, Brain Res. Brain Res. Protoc. 4:185-91. To quantify the cerebral blood vessel density and examine the vascular remodeling by macrophage, each rat was anesthetized with chloral hydrate and perfused with 4% paraformaldehyde. Histological sections (6 µm) were obtained and stained with specific antibody to CD-31 (1:100, BD Pharmingen), OX-42 (1:400, Serotec) or ED-1 (1:500, Serotec) that was conjugated with Cy-3 (1:500, Jackson Immunoresearch PA USA). The number of blood vessels was determined by the method described in Taguchi et al. 2004, J. Clin. Invest. 114:330-8.

The results demonstrate that several bisbenzimide-labeled cells showed vascular phenotypes (positive for vWF) around the perivascular and endothelial regions of the ischemic hemispheres in the treated rats. It was also found that the transplantation in the treated rats significantly enhanced cerebral microvascular perfusion of FITC-dextran in comparison with control rats (n=6). Measurement of blood vessel density examined by anti-CD31 staining showed that the treated rats (n=4) showed significantly more neovasculatures in the penumbric area than the control rats (n=4).

Double immunofluorescent staining and FITC-dextran perfusion were also performed to demonstrate the association between angiogenesis and macrophage/microglial (MA/MI). The total number of positive MA/MI per section was determined according to the method described in Pipp et al., 2003, Circ. Res. 92:378-85. It was found that the transplanted cells (bisbenzimide-labeled) showed macrophage/microglia (MA/MI) phenotypes (OX-42$^+$ and ED-1$^+$) and infiltrated around the perivascular regions (FITC-dextran perfused vessels) of the ischemic hemispheres. Also, the treated rats had more MA/MI around vessels than the control rats.

Western blot was performed to examine β1-integrin expression using specific antibody against β1-integrin (Chemicon). It was found that the level of β1-integrin in the treated rats (n=4) was significantly higher than that in the control rats (n=4). The above-described MCA ligation and transplantation/mock-translation experiments were repeated on rats except that a synthetic cyclic RGD peptide was injected into the ischemic brain. The rats were subjected to the neurological behavior evaluation in the manner described above. It was found that both the expression of β1-integrin and the neurological behavior showed no significant difference between the treated group and control group (n=4 for each group). These results suggest that cyclic RGD peptides block β1-integrin activation and that β1-integrin is involved in the effects of the transplantation.

EXAMPLE 8

An increased vessel density would enhance neuronal survival and is associated with an increased cerebral blood flow (CBF), which would result in efficient delivery of oxygen and neutrients. To examine the CBF in the ischemic brain, the above-described treated and control rats were injected with diamox and monitored by laser doppler flowmetry (LDF) under anesthesia.

Briefly, the rats were positioned in a stereotaxic frame. A baseline local cortical blood flow (bCBF) was measured continuously with a laser doppler flowmeter (LDF monitor, Moore Instrument England) in an anesthetized state according to the method described in Tuettenberg et al., 2001, Neurosci. Lett. 315:65-8. The reactive cerebral blood flow (rCBF) was examined after intraperitoneal injection of 50 mg/kg acetazolamide (Diamox, Lederle) and defined as percentage changes of bCBF. The results showed a significant increase in rCBF in the middle cerebral artery cortex of the ischemic brain in the treated rats compared with the control rats.

EXAMPLE 9

Blood-brain barrier (BBB) integrity was assessed in the above-described rats at Day 28 after the transplantation. Each rat was administered with $10^4$ U/kg of type II horseradish peroxidase (HRP, Sigma) intravenously for thirty minutes and examined for the HRP activity in the manner described in Ferrari, 2004, Am. J. Pathol. 165:1827-1837. It was found that the cell transplantation facilitated repair of injured blood-brain-barrier.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of treating stroke, comprising
identifying a human subject in need thereof, and
administering intracerebrally to the subject an effective amount of a composition containing cultured olfactory ensheathing progenitor cells, olfactory ensheathing cells, or olfactory nerve fibroblasts, wherein the cell composition is prepared by a process including:
obtaining a tissue from a nasal polyp of a human,
culturing the nasal polyp tissue in a medium containing a B27 medium supplement, fetal calf serum (FCS), and an antibiotic for 5-7 days to allow for migration of the cells from the cultured tissue, and
collecting the migrated cells to acquire the cell composition, wherein the cells thus collected are p75$^+$, S100$^+$, or GFAP$^+$.

2. The method of claim 1, wherein the nasal polyp tissue is cultured in a DMEM/F12 medium containing a B27 medium supplement, 10% FCS, and 1% (100 U/ml) penicillin/streptomycin.

3. The method of claim 1, wherein the olfactory ensheathing progenitor cells, olfactory ensheathing cells, or olfactory nerve fibroblasts, are autologous to the human subject.

4. The method of claim 1, wherein the nasal polyp tissue is cultured under 5% $CO_2$ at 37° C. and left undisturbed for 5-7 days to allow for migration of the cells from the tissue.

5. The method of claim 1, wherein, prior to the collecting step, the migrated cells are passaged once a week for three to four weeks and then collected to acquire the cell composition.

6. The method of claim 1, wherein the cell composition is prepared by the process including:
obtaining nasal polyp tissue from a human,
culturing the nasal polyp tissue in a DMEM/F12 medium containing a B27 medium supplement, 10% FCS, and 1% (100 U/ml) penicillin/streptomycin in a flask coated with poly-L-lysine, incubated under 5% $CO_2$ at 37° C., and left undisturbed for 5-7 days to allow for migration of the cells from the cultured tissue,
passaging the migrated cells once a week for three to four weeks, and
collecting the cells produced in the passaging step to acquire the cell composition.

7. The method of claim 6, wherein the cell composition is autologous to the human subject.

* * * * *